(12) United States Patent
Hoctor et al.

(10) Patent No.: US 7,425,199 B2
(45) Date of Patent: Sep. 16, 2008

(54) METHOD AND APPARATUS FOR ULTRASONIC CONTINUOUS, NON-INVASIVE BLOOD PRESSURE MONITORING

(75) Inventors: Ralph Thomas Hoctor, Saratoga Springs, NY (US); Kai Erik Thomenius, Clifton Park, NY (US); Aaron Mark Dentinger, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 795 days.

(21) Appl. No.: 10/948,434

(22) Filed: Sep. 23, 2004

(65) Prior Publication Data
US 2005/0143640 A1  Jun. 30, 2005

Related U.S. Application Data

(63) Continuation-in-part of application No. 10/749,181, filed on Dec. 30, 2003, now Pat. No. 7,125,383.

(51) Int. Cl.
*A61B 5/02* (2006.01)
*A61B 8/04* (2006.01)
(52) U.S. Cl. ................................. 600/485; 600/438
(58) Field of Classification Search ............ 600/438, 600/453
See application file for complete search history.

(56) References Cited

U.S. PATENT DOCUMENTS

| | | | |
|---|---|---|---|
| 4,669,485 A | 6/1987 | Russell | |
| 5,411,028 A | 5/1995 | Bonnefous | |
| 5,503,156 A | 4/1996 | Millar | |
| 5,758,652 A | 6/1998 | Nikolic | |
| 6,176,832 B1 * | 1/2001 | Habu et al. | 600/485 |
| 6,359,367 B1 | 3/2002 | Sumanaweera | 310/309 |
| 6,491,639 B1 | 12/2002 | Turcott | 600/508 |
| 6,514,211 B1 | 2/2003 | Baura | 600/490 |
| 2004/0230128 A1 * | 11/2004 | Brockway et al. | 600/510 |

OTHER PUBLICATIONS

Pending U.S. Appl. No. 10/749,181, filed Dec. 30, 2003.
Pending U.S. Appl. No. 10/248,022, filed Dec. 11, 2002.
Pending U.S. Appl. No. 10/383,990, filed Mar. 3, 2003.

* cited by examiner

*Primary Examiner*—Robert L. Nasser, Jr.
*Assistant Examiner*—Patricia Mallari
(74) *Attorney, Agent, or Firm*—Fletcher Yoder

(57) ABSTRACT

Ultrasound is used to provide input data for a blood pressure estimation scheme. The use of transcutaneous ultrasound provides arterial lumen area and pulse wave velocity information. In addition, ultrasound measurements are taken in such a way that all the data describes a single, uniform arterial segment. Therefore a computed area relates only to the arterial blood volume present. Also, the measured pulse wave velocity is directly related to the mechanical properties of the segment of elastic tube (artery) for which the blood volume is being measured. In a patient monitoring application, the operator of the ultrasound device is eliminated through the use of software that automatically locates the artery in the ultrasound data, e.g., using known edge detection techniques. Autonomous operation of the ultrasound system allows it to report blood pressure and blood flow traces to the clinical users without those users having to interpret an ultrasound image or operate an ultrasound imaging device.

16 Claims, 10 Drawing Sheets

METHOD AND APPARATUS FOR ULTRASONIC CONTINUOUS, NON-INVASIVE BLOOD PRESSURE MONITORING

CROSS-REFERENCE TO RELATED APPLICATIONS

This application is related to and a continuation-in-part (CIP) application of application U.S. Ser. No. 10/749,181, filed Dec. 30, 2003, now U.S. Pat. No. 7,125,383 in the U.S. Patent and Trademark Office.

BACKGROUND OF THE INVENTION

This invention generally relates to methods and apparatus for continuous, non-invasive monitoring of blood pressure.

A method for the determination of non-invasive beat-by-beat (continuous) systolic and diastolic blood pressure has long been desired in physiological monitoring. With this information, rapid changes in the physiological state of a patient can be much better managed. Automatic blood pressure cuffs can be used for this application, by inflating them as rapidly as is possible; however, this provides blood pressure data only at 1 to 2 minute intervals, and each inflation can be painful for elderly or hypertensive patients.

A very reliable technique for continuously measuring blood pressure is to insert a saline-filled catheter through the patient's vascular system to the point at which it is desired to perform the measurements. The catheter is connected to a pressure sensor, which measures the pressure in the vessel. An alternative method uses a catheter with a pressure sensor at the tip that directly senses the blood pressure. However, these techniques involve making an incision through the patient's skin and inserting the catheter into a blood vessel. As a consequence, this invasive procedure entails some risk of complications for the patient.

An indirect, non-invasive process for continuously measuring blood pressure is based on the pulse transit time (PTT) which is the time required for a blood pressure pulse from the heart to propagate between two points in the arterial system. One apparatus for this technique includes an electrocardiograph that senses electrical signals in the heart to provide an indication when a blood pulse enters the aorta. A pulse oximeter is placed on an index finger of the patient to detect when the blood pressure pulse reaches that location. The pulse transit time between the heart and the index finger is measured and calibrated to the existing blood pressure that is measured by another means, such as by the automated oscillometric method. Thereafter changes in the pulse transit time correspond to changes in the blood pressure. Generally, the faster the transit time the higher the blood pressure. Thus, changes in the pulse transit time can be equated to changes in the blood pressure.

However, the electrocardiograph (ECG) senses electrical signals in the heart, which do not indicate the point in time when the blood pressure pulse actually leaves the heart upon the mechanical opening of the aortic valve. A time interval of varying length, known as the cardiac pre-ejection period (PEP), exists between peaks of the QRS wave of the electrocardiogram signal and the aortic valve opening. The inability of prior pulse transit time-based monitors to account for the cardiac pre-injection period resulted in an inaccurate measurement of the pulse transit time and thus blood pressure.

In addition, changes in the compliance of the blood vessels also affect the pulse transit time. Chronic changes in arterial compliance occur due to aging, arteriosclerosis or hypertension. Arterial compliance can also change acutely due to neural, humoral, myogenic or other influences. Previous monitoring systems have been unable to separate changes due to compliance from changes due to blood pressure. As a consequence, some degree of inaccuracy has existed in calculating blood pressure from the variation of the pulse transit time.

Some previous investigators in the area of continuous, non-invasive blood pressure (CNIBP) monitoring have favored tonometric methods. These methods do not require a blood pressure cuff, but do require some small mechanical device that applies pressure to an artery, along with some kind of vibration sensor for tonometric pressure estimation. Such a device is described in published U.S. patent application Publ. No. 2003/0149369 A1. Devices of this type have proven unreliable in practice.

Still other previous investigators have used formulas derived from the Bramwell-Hill equation. These formulas relate blood pressure to measured arterial pulse wave velocity (PWV) and measured arterial blood volume. When the heart beats, it sends a pulse of pressure through the arterial system. This pulse propagates through the system by distending the elastic walls of the arteries, and this mechanism can be approximately represented by a linear wave equation. Due to the dependence of PWV on the elastic expansion of the arterial walls, it is indicative of the local elastic state of the arterial segment. The elasticity of the arteries changes with short-term physiological state. The mean arterial elasticity changes with age, and may be indicative of arterial disease. Stiffening of the arteries can produce systemic hypertension. Thus, the PWV has the potential to provide diagnostic information about the state of the arterial segment being investigated and may also be indicative of overall arterial health. In addition, the PWV changes with the mean radius of the arteries; thus the PWV can be indicative of blood pressure, since higher pressures will result in greater mean arterial distension, all else being equal.

The basic expression for phase velocity of arterial pulse pressure waves is the same as that for the phase velocity of electrical waves propagating in a cable or transmission line, which has the same form of wave equation. The velocity is $$v_p = \sqrt{\frac{1}{LC}} \tag{1}$$

where $v_p$ is the phase velocity of the arterial pulse pressure wave. For cable waves, C is capacitance and L is inductance. For arterial pulse wave propagation, C is called the compliance of the artery, defined as the derivative of the lumen area with respect to the pressure, and is given by $$C = \frac{dA}{dP} = \frac{2\pi r^3}{Eh} \tag{2}$$

where A is the area of the arterial lumen, P is the pressure, r is the radius of the arterial lumen, h is the thickness of the arterial wall, and E is the modulus of elasticity of the arterial wall. This expression for C is derived in many standard textbooks, such as *Hemodynamics, 2d edition*, pages 96-98, by W. R. Milnor, published by Williams & Wilkins, 1989. L, which represents the inertia of the blood that opposes the pressure pulse, is given by $$L = \frac{\rho}{\pi r^2} \quad (3)$$

where $\rho$ is the density of blood. If we substitute Eqs. (2) and (3) into Eq. (1), we get the famous Moens-Korteweg equation:

$$v_p = \sqrt{\frac{Eh}{2r\rho}} \quad (4)$$

If one substitutes Eq. (3) and the definition of C as a derivative into Eq. (1), we get what is called the Bramwell-Hill equation:

$$v_p = \sqrt{\frac{\pi r^2}{\rho} \frac{dP}{dA}} \quad (5)$$

From this equation one can obtain a formula that linearly scales a measured arterial area into a pressure, with the slope based on measured PWV. If one puts all the pressure terms on one side and all the area terms on the other side ($\rho$ is a constant) and then integrates, one gets:

$$P(t) - P(0) \cong \rho v_p^2 \ln\left(\frac{A(t)}{A(0)}\right) \quad (6)$$

Equation (6) is an approximation because the pulse wave velocity is a function of the arterial radius, and therefore the lumen area, and in the derivation of Eq. (6) it was assumed that $v_p$ is a constant with respect to A. It is also possible to use a linearized version of Eq. (6), given by:

$$P(t) - P(0) \cong \frac{\rho v_p^2}{A(0)}(A(t) - A(0)) \quad (7)$$

In order to use Eq. (6) or (7) to generate P(t), the arterial pulse wave velocity (PWV) $v_p$ and the arterial (i.e., lumen) area A must be measured. In addition, the initial values P(0) and A(0) must be obtained, and the blood density, $\rho$, must be replaced with a constant computed from cuff pressure data and ultrasound area and PWV measurements, all of which constitutes a calibration step.

In previous methods, PWV measurements were typically taken by observing the pulse transit time between two widely separated sites, such as the heart and a fingertip. The pulse arrival times at the measurement sites are typically determined by impedance plethysmography or pulse oximetry. In one known prior method (disclosed in U.S. Pat. No. 5,857, 975), the time of the pressure pulse's origin at the heart is determined from an EKG signal. The required area measurements can also be obtained from plethysmography: volume measurements can be turned into areas by assuming a length. The initialization data can be obtained from a pressure cuff. The latter two measurements are not always used, however.

There are also methods that use only pulse wave velocity; because these methods do not measure blood volume/area, they must use empirical relationships between PWV and blood pressure rather than Eq. (6) or (7). One such method is described in published U.S. patent application Ser. No. 2003/0167012.

In the scheme described in U.S. Pat. No. 5,857,975, measurement of area and calibration are replaced by use of an assortment of seemingly arbitrary factors. (This only highlights the fact that schemes that estimate blood pressure on the basis of PWV alone have no physical justification.)

There are several grounds on which existing blood pressure measurements that could be used in Eq. (6) might be criticized. One such criticism concerns the measurement of arterial blood volume. In particular, measurement of arterial area by plethysmography is confounded by the highly elastic nature of the veins. Impedance plethysmography measures total blood volume, and it is often applied to a limb such as the arm or leg. Since this measurement includes the venous blood volume, it cannot be reliably processed to produce arterial lumen area. If the venous blood volume did not change, then it might be possible to calibrate for this effect, but the venous blood volume is strongly affected by the subject's position, since hydrostatic pressures can cause pooling of blood in the veins, which are more highly distensible than the arteries.

Another criticism is that the PWV measurement resulting from measurement at widely separated sites is not directly applicable to Eq. (6). The PWV is being used in Eq. (6) to give information on the mechanical properties of the artery; however, the PWV depends not only on the elasticity of the arterial wall, but also on its thickness and the size of the lumen. Any PWV measurement that is made between widely separated sites is actually measuring PWV over a collection of branches of the arterial tree. Because these branches will have varying lumen area, the measured pulse transit time will reflect a composite of the component pulse wave velocities, and so it will not accurately reflect the mechanical properties of any particular arterial segment. It is possible to regard such a measurement as an approximation, but since Eq. (6) applies to a uniform, cylindrical tube, errors are inevitable, and their magnitude is hard to predict.

Another criticism concerns the way in which the PWV measurements are made. The PWV that is needed in Eq. (6) is that which would be observed in a very long, uniform tube, where there would be no reflections. In contrast, the human arterial system is a complex tree of branching arteries starting with the largest artery, the aorta, and ending with the smallest vessels, the capillaries. In addition to the diameter decreasing as the distance increases away from the heart, the elastic properties of the artery also change with location in the arterial tree. Thus, the PWV is also dependent on the location at which it is measured and typically increases with distance from the heart. Bifurcation sites represent an abrupt change in diameter and hence a change in the propagation speed of the pressure pulse wave. Due to this change, the bifurcations are sources of reflections causing a pressure pulse to be reflected back towards the heart. The pressure at any point in the arterial system is the combination of the pressure from the forward traveling pressure pulse and all the reflections traveling past the measurement site. The presence of the reflected pulse waves makes measurement of pulse wave velocity difficult. Since the wavelength of the pressure pulse is so long, the reflection has the effect of shifting those features of the waveform (such as the maximum value) that might be used as markers in measuring the pulse transit time between two observation points.

A more fundamental criticism of blood pressure estimation based on Eq. (6) is that changes in physiological state can bring about changes in arterial wall elasticity. In general, this will change the measured PWV, and so the model of Eq. (6) will, to some extent, adapt to such changes. However, the operating point (P(0), A(0)) also depends on this elasticity, as does any multiplicative constant used to replace ρ. If the elastic modulus of the wall changes, then the same pressure will be associated with a different area. If the operating point and calibration constant are obtained using a pressure cuff calibration, then any changes of arterial elasticity would in principle require re-calibration, and if no such re-calibration is done, then gross errors in pressure estimation can occur. For example, if the mean pressure goes down while the elasticity goes up (which means that the elastic modulus E goes down), then the mean area could also go up. In that case, without an adjustment of (P(0), A(0)), the mean of the estimated pressure would go up rather than down.

There is a need for a method and means for acquiring data for use in the above-described blood pressure estimation scheme that overcomes the aforementioned drawbacks of prior art systems.

BRIEF DESCRIPTION OF THE INVENTION

The present invention overcomes the aforementioned drawbacks. In a disclosed embodiment, a system for monitoring of pressure in a lumen comprises an image acquisition system, data processor and means for delivering signals derived from the output of the image acquisition system to the data processor. The data processor is programmed to perform the following steps: (a) converting acquired disturbance propagating waveform information corresponding to energy transmitted and returned from a lumen wall, flow through the lumen and adjacent areas surrounding the lumen, into electrical signals; (b) forming at least one spatial covariance matrix of frequency components the propagating waveform measured at a plurality of locations along the lumen; (c) processing the at least one spatial covariance matrix to estimate a velocity of a pulse wave and any reflections traveling through the lumen; and, (d) computing the pressure as a function of the estimated velocity.

One aspect of the invention is a method for monitoring pressure in a lumen, comprising the following steps: (a) converting acquired disturbance propagating waveform information corresponding to energy transmitted and returned from a lumen wall, flow through the lumen and adjacent areas surrounding the lumen; (b) forming a spatial covariance matrix of frequency components of the propagating waveform; (c) processing the spatial covariance matrix to estimate the velocity of a pulse wave and any reflections through the lumen; and, (d) computing the pressure as a function of the estimated velocity.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

Figure 1:
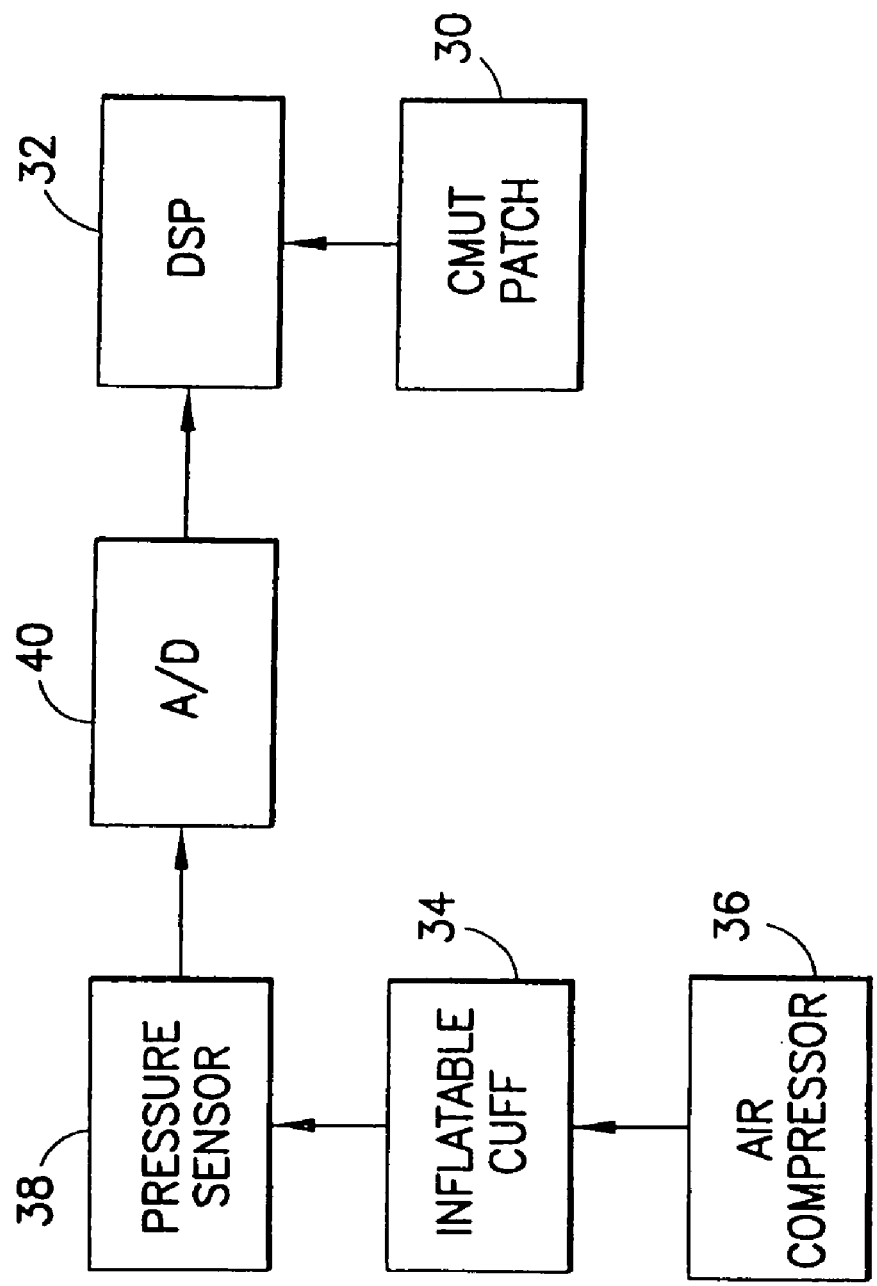
FIG. 1 is a block diagram of a CNIBP measurement system in accordance with one embodiment of the invention.

In accordance with embodiments of the invention disclosed herein, ultrasound is used to provide input data for the blood pressure estimation scheme. The use of transcutaneous ultrasound can provide volumetric flow, arterial lumen area and pulse wave velocity information. In addition, ultrasound measurements can be taken in such a way that all the data describes a single, uniform arterial segment (e.g., the brachial and common carotid arteries can be used). This means that a computed area relates only to the arterial blood volume present. This also means that the measured PWV is directly related to the mechanical properties of the segment of elastic tube (artery) for which the blood volume is being measured. In the patient monitoring application, the operator of the ultrasound device is eliminated through the use of software that automatically locates the artery in the ultrasound data, e.g., using known edge detection techniques. Autonomous operation of the ultrasound system allows it to report blood pressure and blood flow traces to the clinical users without those users having to interpret an ultrasound image or operate an ultrasound imaging device.

The use of ultrasound measurements in the continuous blood pressure monitoring application is enabled by micromachined ultrasonic transducer patch probe technology, which allows ultrasound data to be taken using a thin, lightweight probe that adheres to the patient's skin. Recently semiconductor processes have been used to manufacture ultrasonic transducers of a type known as micromachined ultrasonic transducers (MUTs), which may be of the capacitive (cMUT) or piezoelectric (pMUT) variety. cMUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave.

One advantage of MUTs is that they can be made using semiconductor fabrication processes, such as microfabrication processes grouped under the heading "micromachining". As explained in U.S. Pat. No. 6,359,367:

> Micromachining is the formation of microscopic structures using a combination or set of (A) Patterning tools (generally lithography such as projection-aligners or wafer-steppers), and (B) Deposition tools such as PVD (physical vapor deposition), CVD (chemical vapor deposition), LPCVD (low-pressure chemical vapor deposition), PECVD (plasma chemical vapor deposition), and (C) Etching tools such as wet-chemical etching, plasma-etching, ion-milling, sputter-etching or laser-etching. Micromachining is typically performed on substrates or wafers made of silicon, glass, sapphire or ceramic. Such substrates or wafers are generally very flat and smooth and have lateral dimensions in inches. They are usually processed as groups in cassettes as they travel from process tool to process tool. Each substrate can advantageously (but not necessarily) incorporate numerous copies of the product. There are two generic types of micromachining . . . 1) Bulk micromachining wherein the wafer or substrate has large portions of its thickness sculptured, and 2) Surface micromachining wherein the sculpturing is generally limited to the surface, and particularly to thin deposited films on the surface. The micromachining definition used herein includes the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides.

The same definition of micromachining is adopted herein. The systems resulting from such micromachining processes are typically referred to as "micromachined electromechanical systems" (MEMS).

The use of a MUT patch allows the clinician to stick the transducer to the patient's skin. The MUT patch is lightweight and flat. For the purpose of illustration, a transducer patch will be described that is made up of capacitive micromachined ultrasonic transducers (cMUTs). However, it should be understood that the patch could instead employ pMUTs. An embodiment will now be described that incorporates a MUT patch. However, it should be understood that the present invention encompasses not only a device, but also methods for continuous non-invasive blood pressure monitoring, and that the basic method is not limited in their application to devices that employ MUT technology. Instead, the basic method disclosed and broadly claimed herein can also be performed by appropriately programmed ultrasound imaging systems having probes comprising conventional piezoceramic transducer elements.

It is to be appreciated that systems other than ultrasound imaging systems may benefit from the methods described herein. Further, applications other than blood pressure monitoring, such as but not limited to arterial schlerosis and arterial blockage diagnosis and monitoring, are also contemplated. Image date acquisition by an ultrasound imaging system for the purpose of blood pressure monitoring is provided as an exemplary embodiment, but it is contemplated that image data acquisition may be by other imaging systems (e.g. high frame rate imaging modalities such as magnetic resonance imaging (MRI), computed tomography (CT) and fluoroscopic X-ray imaging). Further, medical and industrial applications that measure flow, diameter, and pressure of lumen other than arteries and arterial segments may also benefit from the methods described herein. As used herein, the terms artery, arterial walls, vessels, etc. used herein are exemplary embodiments and are not intended to limit the invention. Further, as used herein, the term "lumen" refers to an elastic, tubular structure having an anterior wall and a posterior wall and may contain an inner volume capable of holding a flowing substance. A lumen may comprise an artery, arterial walls or vessel, but also comprise an industrial structure such as a pipe or tube.

FIG. 1 shows a simplified representation of a system for accomplishing the foregoing in accordance with one embodiment of the invention. A cMUT patch 30 is attached to the patient's skin with an adhesive and an inflatable cuff 34 is placed around one of the patient's arms. The patch is placed on the underside of the arm or in some other spot that gives it access to an artery that is relatively near the skin. The patch 30 is connected to a portable personal computer by a cable (not shown). The portable PC is small enough to be strapped to the patient.

Based on acoustic data from the cMUT patch 30 and pressure data from the cuff 34, a digital signal processor (DSP) 32 [incorporated in the portable PC} autonomously computes various parameters, including the patient's estimated blood pressure. In addition, the DSP software forms and steers ultrasound beams over the volume of space in front of the cMUT patch 30. Using both echo intensity and Doppler blood flow information, the software maps out the location of the vessel, its cross-sectional area, and the area increase at the time of passage of the systolic pressure wave. The pulse wave velocity can also be measured. This will yield useful information about the mechanical properties of the blood vessel wall.

For this reason, the cuff 34 is periodically inflated by the DSP 32 to provide the peak and steady state pressures at fixed points in time. More specifically, the DSP activates an air compressor 36 to inflate cuff 34. A pressure sensor 38 detects the pressure in the cuff 34. The analog output of the pressure sensor 38 is converted to a digital value by an analog-to-digital converter 40, which digital pressure value is used by the DSP 32. Initially the DSP triggers cuff inflation in response to an activation command input by the system operator via an operator interface (not shown) of the portable PC. Thereafter, the DSP triggers re-inflation of the cuff whenever the estimated compliance value changes by more than a threshold. [The compliance is measured/estimated using arterial pulse wave velocity and mean arterial area using an algorithm that will be described later in detail.] The results of the computations are displayed on a display screen (not shown) of the portable PC.

Although the pressure sensor and the transducer array in the disclosed embodiment are electrically coupled to the processor (or processors) by means of cables, obviously a wireless electrical coupling could be provided.

Figure 2:
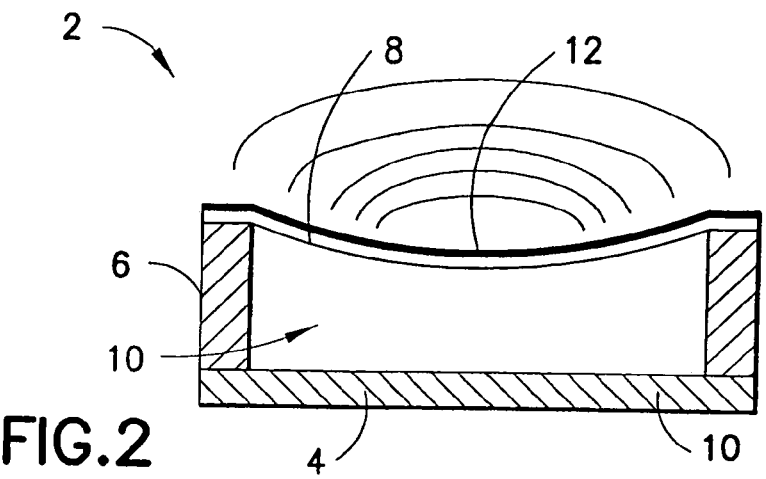
FIG. 2 is a drawing showing a cross-sectional view of a typical cMUT cell.

Referring to FIG. 2, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 16 between the membrane 8 and the substrate 4 may be air- or gas-filled or wholly or partially evacuated. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the semiconductive substrate 4.

The two electrodes 10 and 12, separated by the cavity 16, form a capacitance. When an impinging acoustic signal causes the membrane 8 to vibrate, the variation in the capacitance can be detected using associated electronics (not shown in FIG. 2), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

Figure 3:
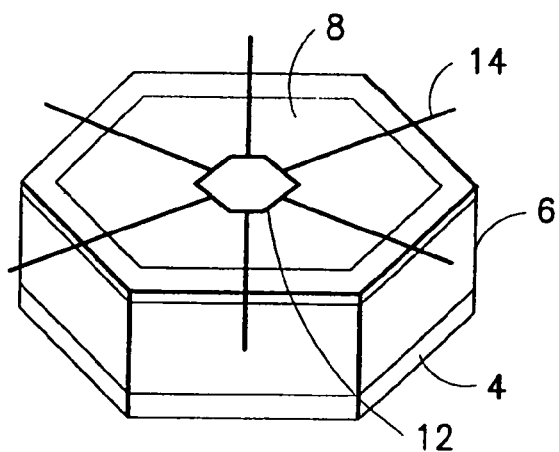
FIG. 3 is a drawing showing an isometric view of the cMUT cell shown in FIG. 2.

The individual cells can have round, rectangular, hexagonal, or other peripheral shapes. A cMUT cell having a hexagonal shape is shown in FIG. 3. Hexagonal shapes provide dense packing of the cMUT cells of a transducer subelement. The cMUT cells can have different dimensions so that the transducer subelement will have composite characteristics of the different cell sizes, giving the transducer a broadband characteristic.

Unfortunately, it is difficult to produce electronics that would allow individual control over such small cells. While in terms of the acoustical performance of the array as whole, the small cell size is excellent and leads to great flexibility, control is limited to larger structures. Grouping together multiple cells and connecting them electrically allows one to create a larger sub-element, which can have the individual control while maintaining the desired acoustical response. So a sub-element is a group of electrically connected cells that cannot be reconfigured. For the purpose of this disclosure, the sub-element is the smallest independently controlled acoustical unit. One can form rings or elements by connecting sub-elements together using a switching network. The elements can be reconfigured by changing the state of the switching network. However, sub-elements are hardwired into the design and cannot be reconfigured.

Figure 4:
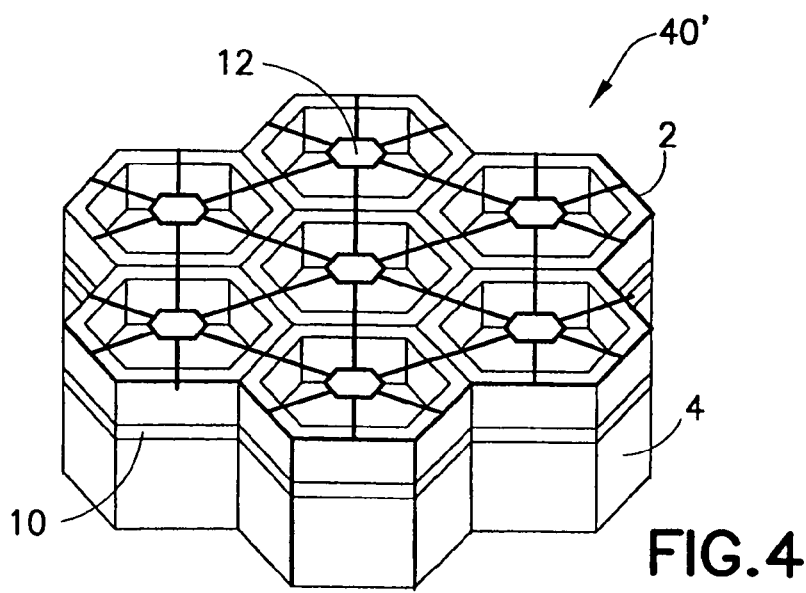
FIG. 4 is a drawing showing an isometric view of a "daisy" sub-element formed from seven hexagonal cMUT cells having their top and bottom electrodes respectively hard-wired together.

For the purpose of illustration, FIG. 4 shows a "daisy" transducer sub-element 24 made up of seven hexagonal cMUT cells 2: a central cell surrounded by a ring of six cells, each cell in the ring being contiguous with a respective side of the central cell and the adjoining cells in the ring. The top electrodes 12 of each cell 2 are hard-wired together. In the case of a hexagonal array, six conductors 14 (shown in both FIGS. 3 and 4) radiate outward from the top electrode 12 and are respectively connected to the top electrodes of the neighboring cMUT cells (except in the case of cells on the periphery, which connect to three, not six, other cells). Similarly, the bottom electrodes 10 of each cell 2 are hard-wired together, forming a seven-times-larger capacitive transducer sub-element 24.

Figure 5:
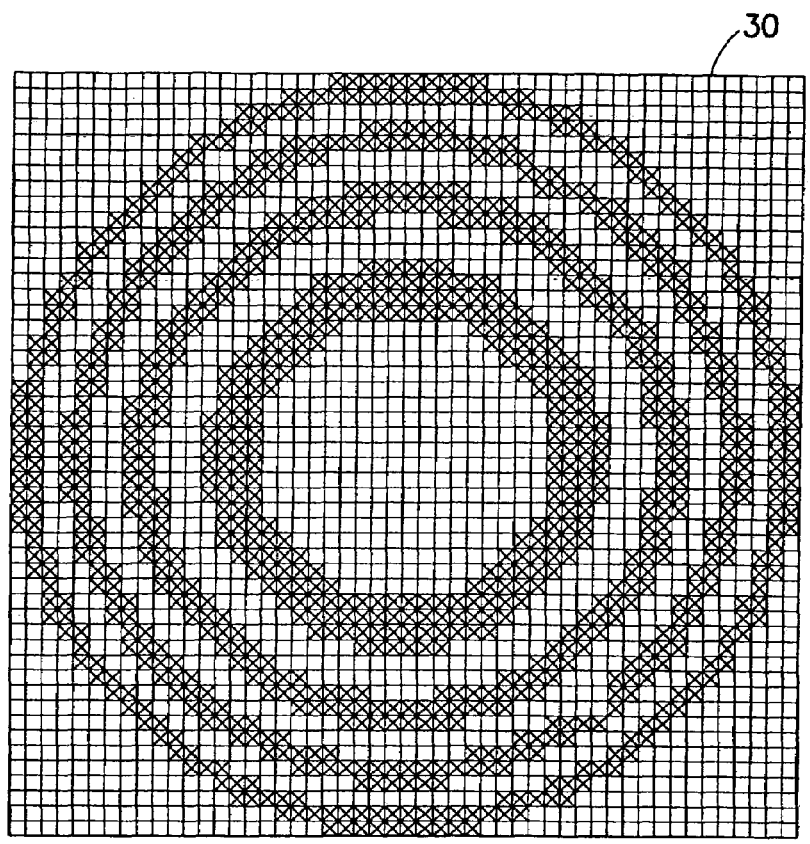
FIG. 5 is a drawing showing a mosaic array comprising eight annular elements.

Sub-elements of the type seen in FIG. 4 can be arranged to form a two-dimensional array on a semiconductive (e.g., silicon) substrate. These sub-elements can be reconfigured to form elements, such as annular rings, using a switching network. FIG. 5 is a drawing showing a mosaic array comprising eight annular elements. The drawing has been simplified by representing each subelement as a square, although it should be understood that the subelements could be of the type shown in FIG. 4.

Reconfigurability using silicon-based ultrasound transducer sub-elements was described in U.S. patent application Ser. No. 10/383,990. One form of reconfigurability is the mosaic annular array, also described in that patent application. The mosaic annular array concept involves building annular elements by grouping sub-elements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those sub-elements with common delays and thus the annular array is born. The reconfigurability can be used to step the beam along the larger underlying two-dimensional transducer array in order to form a scan or image.

Figure 6:
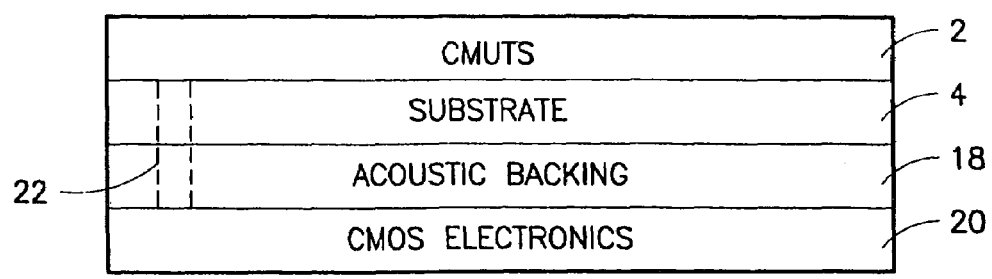
FIG. 6 is a drawing showing the construction of a cMUT patch in accordance with one embodiment of the invention. In the depicted example, the cMUT cells have been surface micromachined on the substrate. However, the cMUT cells could alternatively be bulk micromachined on the substrate, in which case the solid line at the interface of the cMUT and substrate layers could be changed to a dashed line.

In accordance with one embodiment of the present invention shown in FIG. 6, an array of cMUT sub-elements is built on one silicon wafer and conventional metal oxide semiconductor (CMOS) switches and preamplifier/buffer circuits are formed on a second silicon wafer to provide a cMUT patch having reconfigurable beamforming elements. An acoustic backing layer 18 is preferably sandwiched between the cMUT wafer 2/4 and the CMOS wafer 20 with vias 22 for passage of electrical connections between the wafers.

The acoustic backing material 18 should have a composition that is acoustically matched to the cMUT substrate 4, to prevent reflection of the acoustic energy back into the device. In the case where the substrate is made of silicon, one example of a suitable backing material comprises a mixture of 96.3% (by mass) tungsten (of which 85% was 10 micron and 15% was 1 micron particle size) and 3.67% polyvinyl chloride (PVC) powders, as disclosed in U.S. patent application Ser. No. 10/248,022 entitled "Backing Material for Micromachined Ultrasonic Transducer Devices". The person skilled in the art will recognize that the composition of the acoustic backing material can be varied from the example given above, However, the acoustic impedance of the resulting backing material should be matched to that of substrate material. For example, if the substrate is silicon, the acoustic impedance should be approximately 19.8 MRayls±5%.

The CMOS electronics preferably includes the transmit and receive circuits (including a respective transmit/receive switch for each cMUT sub-element) and at least a portion of the beamforming circuits. The CMOS electronics also include switches that enable reconfiguration of the sub-elements, allowing an aperture to be translated over the two-dimensional active area of the transducer. The shape of the apertures is determined by the desired steering angle for the ultrasound beam.

For the autonomous blood pressure monitoring application, the artery will have to be identified without any intervention from an operator once the patch has been placed on the patient. The artery can be initially identified using the typical acquisition modes for color flow imaging available on current ultrasound machines. The color flow imaging is well suited for the task of highlighting the pulsating blood flow in a larger artery and can be used along with the B-Mode images to provide an initial location of the artery for further tracking during the measurements.

Figure 7:
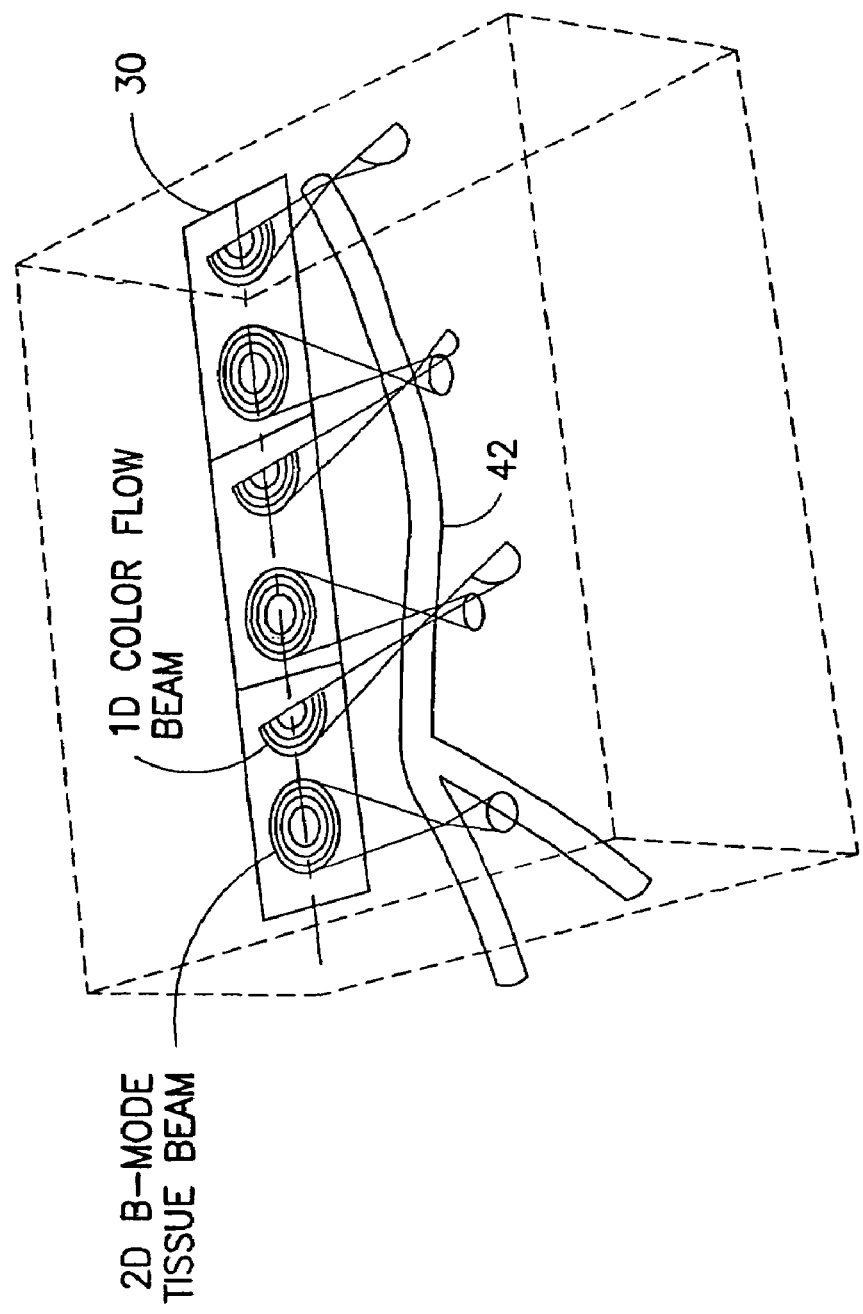
FIG. 7 is a drawing showing the CNIBP measurement concept in accordance with the disclosed embodiment of the invention.

Once an artery has been identified, two types of data are acquired simultaneously using the cMUT patch, as shown in FIG. 7. The first data type is a sequence of B-mode images providing several short-axis views of the lumen (artery in this figure) 42 (in planes perpendicular to the direction of blood flow). Two or more short-axis views are taken along the length of the artery. The system processor can find the center of the artery automatically at each measurement location using edge detection techniques. The center of the artery can then be estimated by the system processor for any location along the length of the patch using interpolation. In addition to finding the artery center, the B-mode data is used to estimate the vessel diameter for the blood pressure calculation. More specifically, it is assumed that that the cross section of the lumen is a circle, so the estimated diameter can be used to calculate the lumen area A, which is then plugged into Eq. (6) or (7).

The second data type is a set of M-mode lines to be used for Doppler processing. The M-mode lines are steered to intersect the center of the artery using information from the B-mode data. This beamsteering is done automatically by the system processor without operator intervention. For each M-mode line to be directed at locations along the artery that lie between B-mode planes, the beam-steering angle is adjusted by interpolating the B-mode arterial location data derived from those two B-mode image planes. The M-mode beams stay locked on the artery across the patch and in real time. The multiple M-mode lines can be used with no Doppler steering angle for determining the velocity of the vessel wall or with a Doppler steering angle for determining blood velocities. The M-mode data, either wall or blood velocities, will be used for estimating the pulse wave velocity needed for the blood pressure calculation.

The two types of data are acquired by interleaving the acquisitions, possibly at different data rates, of the short-axis B-mode beams and the Doppler M-mode beams. An example of a repeating scan sequence for acquiring the data could consist of a single B-mode beam at each location and all the M-mode beams. In the next pass through the sequence, the B-mode beams are translated across the patch while the M-mode beams remain in the same position. This is repeated until the desired width for the B-mode image is covered, generating a single frame of the B-mode data. Then the steps are repeated using any updated information about the vessel center. The result of the acquisition is M-mode data at a high repetition rate (~2 kHz), as required for Doppler processing, and the B-mode images at a slower rate (~100 Hz) determined by the required image size for automatic vessel tracking.

Figure 8:
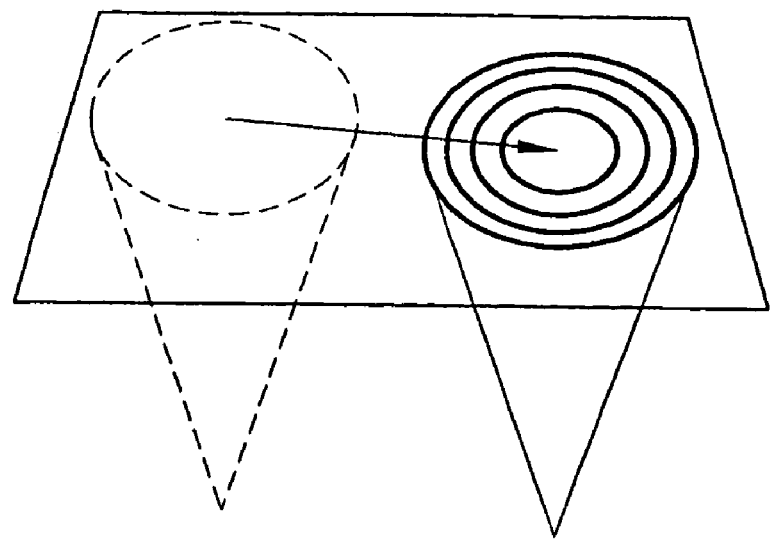
FIG. 8 is a drawing showing scanning of an ultrasound beam, which can be repeated frequently to generate a rectilinear two-dimensional image.

The B-mode beams are translated across the cMUT patch by translating the annular array of activated sub-elements (seen in FIG. 5) across the patch as shown in FIG. 8. A uniform translation of the beamforming coefficients produces a new beam at a different location. Repeated frequently, this generates a rectilinear two-dimensional image.

Figure 9:
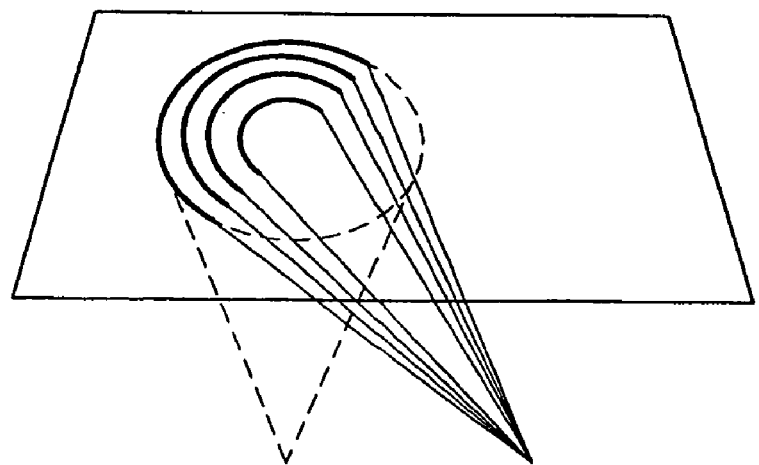
FIG. 9 is a drawing showing steering of an ultrasound beam away from the normal.

An additional bilinear term in the beamforming coefficients produces a beam directed away from the normal, as seen in FIG. 9. Such beams are transmitted in the M mode to acquire data for Doppler processing that computes the blood velocity based on the Doppler effect.

M-mode beams that are transmitted generally normal to the artery are used to acquire data for Doppler processing of the arterial wall velocity during deflection of the wall as the pulse wave travels down the artery. The maximum deflection occurs when the wall velocity is zero.

Blood pressure estimation is performed using a modified version of Eq. (7):

$$P(t) \cong K_1\left(\left(\frac{v_p(t)}{v_p(0)}\right)^2 - 1\right)P_s(0) - \frac{K_2 v_p^2(t)}{A_m(0)}(A_s(t) - A(t)) \quad (7')$$

In this formula, P(t) represents the estimated pressure at the time of the ultrasound measurements, $v_p(t)$ represents the estimated pulse wave velocity derived from the ultrasound measurements, and $A_s(t)$ is the estimated average arterial area at systole from ultrasound measurements. A(t) can either be the instantaneous arterial area measured from ultrasound or the average area during some part of the heart cycle, such as diastole; in either case, P(t) is the corresponding blood pressure. The quantities identified with time zero are derived from the blood pressure cuff and from ultrasound measurements performed at the time of cuff inflation. The inflatable cuff measures systolic, diastolic and mean blood pressure over a period of 20 to 30 heartbeats. The measured systolic (maximum) blood pressure is $P_s(0)$ in Eq. (7'). Excursions of the lumen area A are detected using ultrasound to obtain the mean lumen area $A_m(0)$ in Eq. (7'). Pulse wave velocity is estimated using methods described in detail below. The calibration blood pressure and the calibration lumen area and pulse wave velocity need not be measured concurrently. For example, the mean blood pressure can be measured over a span of 20 to 30 heartbeats and then the mean lumen area and pulse wave velocity can be measured over the next 20 heartbeats. The value of $K_2$ is computed so that the equation $$P_{systolic} - P_{diastolic} \cong \frac{K_2 v_p^2}{A_{mean}}(A_{systolic} - A_{diastolic}) \quad (8)$$

is satisfied for pressure and area measurements taken at nearly the same time.

The term that multiplies $P_s(0)$ in Eq. (7') is there to modify the calibration time systolic pressure using the observed mean pulse wave velocity. This procedure is only valid during periods when the arterial tone does not change, and so this estimation scheme requires the use of the automatic re-calibration procedure described below. At the time of the first calibration, $K_1$ is set to an empirically determined constant. When subsequent automatic re-calibrations occur, $K_1$ is computed as $$K_1 = \frac{v_p^2(0)}{v_1^2(T) - v_0^2(0)} \frac{P_s(T)}{P_s(0)}$$

where the time zero refers to the initial cuff calibration time and the time T refers to the subsequent cuff calibration time.

The lumen area A(t) and the pulse wave velocity $v_p$ are measured to obtain the blood pressure P(t) using Eq. (7'). Measurements of the lumen area will typically be available at a far higher rate than measurements of the PWV.

In order to estimate the instantaneous lumen area, it is assumed that the lumen is circular. The problem to solve is to determine the diameter of an artery in a short-axis ultrasound image sequence. In accordance with one embodiment of the invention, a two-dimensional matched filter method is used for estimating vessel diameter. In a short-axis ultrasound image, the lumen of the artery is black with a circular shape when the ultrasound scan plane is perpendicular to the direction of flow and becomes elliptical when the angle deviates from perpendicular. The edge that is seen in the ultrasound image is the boundary between the medial and adventitial layers of the artery. There is also a small portion of edge from the intimal layer, but this is only seen for a small arc near the anterior and posterior locations.

To estimate the diameter from a circular image requires determination of two or more edge locations. If two locations are used, they must be constrained to be on a diameter. If three locations are used, the three parameters of a circle (center x and y location plus radius) can be found. If more than three locations are used, the circle parameter can be found to minimize an error. Similarly, to find the parameters of an ellipse requires four or more edge locations. To determine the diameter from an ellipse would require a correction for tilt of the scan plan from perpendicular.

The embodiment described is a method for finding the edge locations in an ultrasound short-axis image to be used in determining the vessel diameter. The approach is to construct a two-dimensional matched filter or template of the vessel wall at a certain location and then find the location in the image having the maximum correlation to the filter. The matched filter approach is an optimal method, in terms of signal-to-noise ratio, for finding a known signal in the presence of Gaussian white noise. The embodiment applies this concept to the artery wall detection.

Figure 10:
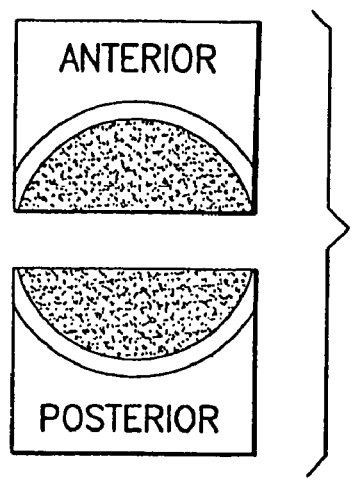
FIG. 10 is a drawing showing examples of matched filters for the anterior and posterior walls of the artery in accordance with one embodiment of the invention.

For the case of a circular-shaped vessel, the artery geometry is parameterized by an approximate diameter and edge thickness. A matched filter is designed to have the desired curvature for a portion of the edge and transition from a low value inside the lumen to a high value at the edge. The coefficients outside the desired edge are set to zero since this corresponds to the outer tissue, which varies significantly in intensity level. The pixel geometry in the image is also used in determining the coefficients of the two-dimensional matched filter. The approach will work for both linear probes that have rectangular pixels and for sector probes with wedge-shaped pixels. Examples of matched filters for the anterior and posterior walls of the artery are shown in FIG. 10.

Using the matched filter designed from the given vessel and pixel geometries, the filter is moved across the image and the correlation of the filter and the image is found at a set of pixel locations. The edge location is found by selecting the pixel with the highest correlation. Refinement of the edge location to sub-pixel accuracy (within a fraction of a pixel) can be performed by several methods. Interpolation could be done on the original image, thereby reducing the pixel size, or the pixel correlations could be fit with a surface and the location of the maximum on the correlation surface could be found more precisely. Another method would be to design a set of poly-phase filters corresponding to sub-pixel offset of the original filter. Correlation of these filters with the image at the current selected pixel could be used to determine the sub-pixel offset with the highest correlation.

Figure 11:
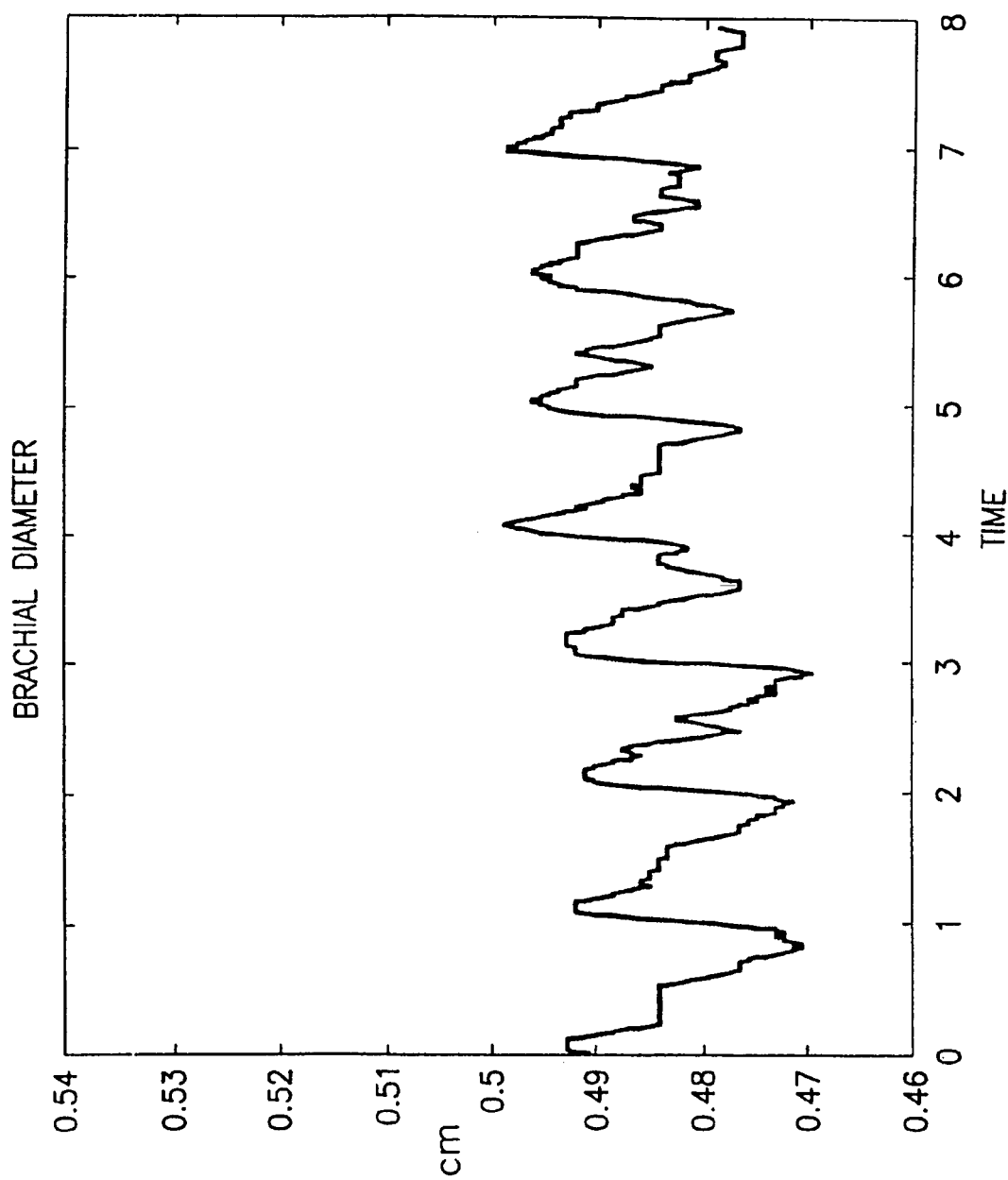
FIG. 11 is a graph showing an example of the diameter estimation using the matched filter technique on a brachial artery.

The output of this method will determine a set of edge locations from which the diameter can be estimated. Since in most applications a sequence of ultrasound frames are acquired, the previous estimates of the diameter can be used to predict the diameter in the current frame and this value can be used to design or select the matched filter. In addition, the previous estimates of the edge locations can be used to predict the position of the edge in the current frame to define a small region of interest over which to search for the edge. An example of the diameter estimation using this technique on the brachial artery is shown in the FIG. 11.

Alternatively, a faster method for estimating the arterial area can be used. This alternative method uses only a single ultrasound line to measure the diameter and estimates the cross-sectional area from the single diameter measurement. This method is less reliable than the matched filtering method described above, but has the following advantages. (1) It is faster to collect the data for a single ultrasound line. (2) When performing the blood pressure estimation on an ordinary ultrasound device with a standard ultrasound probe, the short axis data is not available.

Figure 12:
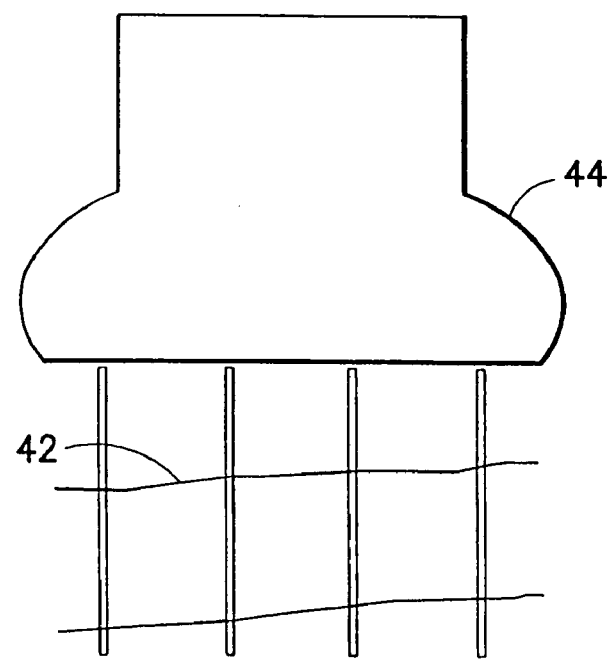
FIG. 12 is a drawing showing long-axis ultrasound data acquisition in accordance with an alternative method of diameter estimation.

This alternative method employs an algorithm that tracks arterial diameter in high-frame-rate long-axis ultrasound B-Mode data. Long-axis data is obtained by positioning the probe face in line with the artery, such that blood travels from one end of the probe face to the other. FIG. 12 is a diagram of a typical long-axis ultrasound data acquisition.

In the case of CNIBP measurement, long-axis data acquisition is done at very high frame rates (~1000 frames per second, or fps). This high frame rate is needed for other necessary measurements, including pulse wave velocity. Since each beam fired requires time to travel the desired depth, reflect, and eventually die out, the number of beams fired and depth imaged will directly impact frame rate. For this reason, only four beams of B-mode ultrasound are fired to achieve ~1000 fps. However, an image is not formed with this type of acquisition; it is equivalent to multiple M-mode lines. FIG. 12 shows how these four beams are distributed.

As shown in FIG. 12, an image is not formed with this high-frame-rate acquisition method, which eliminates the possibility of using adjacent beam information for noise suppression and filtering, as adjacent beams are separated by several millimeters. This is enough spatial distance for the artery to be in a different position and possibly have a slightly different diameter.

Figure 13:
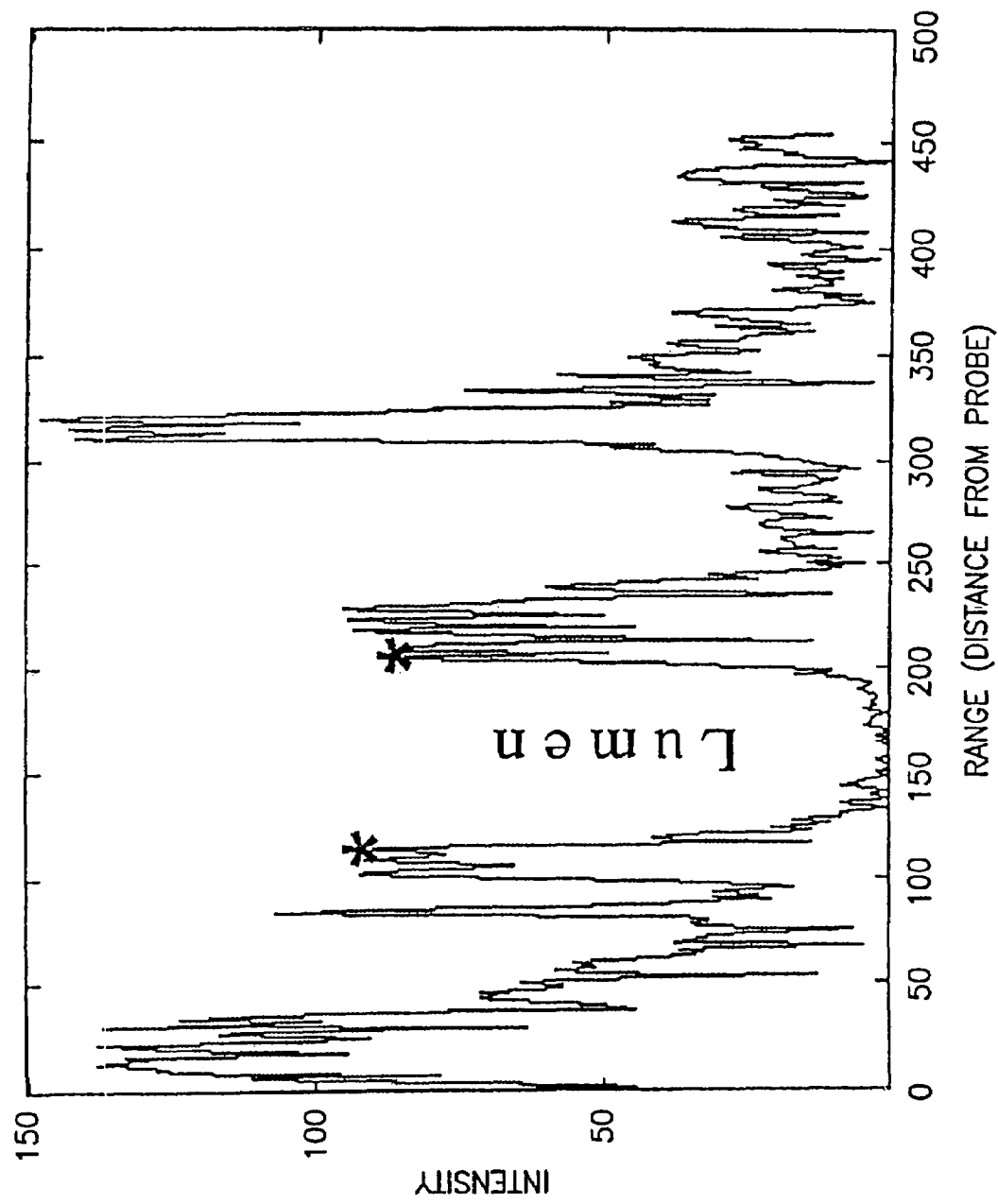
FIG. 13 is a graph of intensity versus range for a single frame of data acquired using long-axis ultrasound data acquisition.

The peak tracking algorithm described herein determines arterial diameter at every frame using a single beam of data. FIG. 13 shows a single frame of this data, B-Mode Intensity vs. Range (i.e., depth). The asterisks (*) in FIG. 13 denote the location of the anterior and posterior walls. At present, these wall locations are first selected manually as initial conditions. The algorithm tracks these locations in time, as described below, to determine arterial diameter for every frame.

Peak Tracking Algorithm

As shown in FIG. 13, the data is inherently very noisy. The first step of the algorithm is to filter with a selectable-size Gaussian window, both spatially (along range) and temporally (along frames). The initial wall locations are identified manually (asterisk locations). Next, the algorithm fits a parabola to each of the initial wall locations and adjoining intensity values. The number of adjoining values used is selectable, but experimental results show a value of 3 (for a total of 7 points; center±3) yields valid parabolas for most datasets. The range location of the maximum of each parabola is evaluated to obtain actual wall positions to sub-pixel accuracy. The difference of the anterior and posterior positions is the arterial diameter.

For successive frames, the sub-pixel position is rounded to the nearest integer location. This is used as the next wall location estimate. It has been experimentally shown that the movement of these parabolic peaks allows the algorithm to follow the arterial wall throughout the cardiac cycle. If the location of the parabolic peak is greater than 3 range samples away from the previous frame's estimate, or if the parabola is concave (indicating an invalid peak), the algorithm reports no movement and continues. This is done to prevent the algorithm from wandering from the actual wall location.

Figure 14:
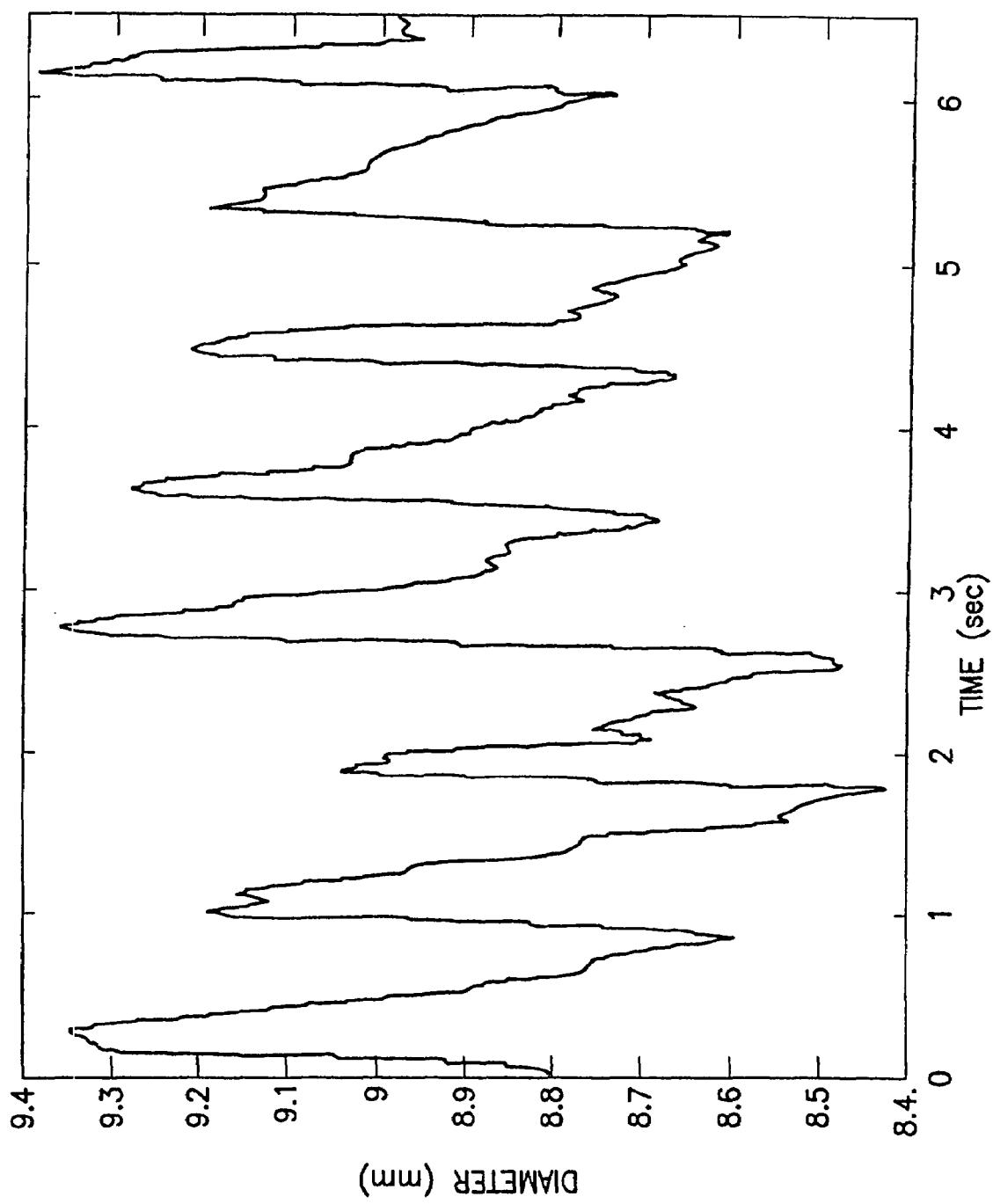
FIG. 14 is a graph showing an example of the diameter output using the peak tracking algorithm disclosed herein.

The sub-pixel distance between anterior and posterior wall locations can be converted to absolute diameter in millimeters using knowledge of the range sampling for the acquisition. Time in seconds can be calculated in the same way using frame rate information. FIG. 14 shows a section of diameter output from the algorithm.

More generally, the blood pressure estimation method should be able to adapt to physiological changes in arterial elasticity, which are part of the body's system for regulation of blood pressure. What is required is a method for sensing when a physiological change is the arterial elasticity has taken place and causing a re-calibration (that is, a cuff inflation). A PWV-based estimate of the arterial compliance C can be used as an indicator of physiological change. The Bramwell-Hill formula [Eq. (5)] gives a relationship between the PWV and the radius, parameterized by C, which is $$C = \frac{K v_p^2}{A} \quad (9)$$

Since PWV and radius (or area) are measured, one can compute and track the estimated value of the compliance. The value of A in this formula is the mean area, and the value of K is computed using Eq. (9). The estimated compliance can be applied to the estimated variation in arterial area to estimate the pulse pressure, which is the difference between the systolic and diastolic pressures. When this estimated pulse pressure value changes by more than a threshold, a cuff inflation is triggered.

However, to compute the compliance used in conjunction with Eq. (9) to govern re-triggering of the blood pressure cuff, the actual pulse wave velocity, unbiased by reflections, is needed. As mentioned earlier, pulse wave reflections occur at every bifurcation and change in lumen radius. These pulse wave reflections can change the apparent (measurable) pulse transit time. In accordance with a further aspect of the present invention, a pulse wave velocity estimation technique is provided based on ultrasound measurements with corrections for reflections.

In accordance with one embodiment of the invention, the DSP (or other processor) is programmed to perform PWV estimation with reflection correction. Processing steps for least-squares, frequency-domain estimation of arterial pulse wave velocity with model-based reflection correction will now be described. This method operates by measuring a disturbance caused by the passage of the arterial pulse pressure wave through an arterial segment. This disturbance could be the distension, or change in size, of the artery; it could be blood flow velocity; or it could be the velocity of the arterial wall. (The easiest technique is to measure wall velocity.) In any case, the measurement will be made at several sites along the length of the arterial segment of interest, and the measurements made at these sites will be processed jointly to obtain a pulse wave velocity estimate. Because the signal processing method is model-based, the disclosure will begin by describing a mathematical model that describes the observed disturbance in terms of the pulse pressure wave and its reflection. This description supplies sufficient background information to make the implementation of the scheme understandable.

A Model of the Disturbance Components

Because the sites of the ultrasound measurement lie along the length of the artery, the disturbance will appear to travel from one site to the next. Because the disturbance signal defined above responds to the pressure pulse, this signal propagates from site to site with the wave speed of the pulse pressure wave. Thus, given the distance along the artery between measurement sites, the relative phases of the set of disturbance signals contain information about the pulse wave velocity. However, the direct measurement of this velocity is prevented by the presence of pulse wave reflections. If there were no pulse wave reflections, it would only be necessary to measure the delay of the disturbance as it propagates between measurement sites. With reflection, the shape of the disturbance changes between measurement sites, making delay estimation difficult. In order to estimate the pulse wave velocity in the presence of reflections, a model-based procedure is used that assumes that a linear reflection with unknown reflection coefficient occurs at a site an unknown distance distal from the most distal ultrasound measurement site.

Suppose that the disturbance is observed at a site that is D millimeters upstream from a reflection site with reflection coefficient $\Gamma$. The total disturbance at that site can then be expressed as the sum of the forward and backward wave components:

$$y(t) = z(t) + \Gamma z\left(t - \frac{2D}{v_p}\right) \quad (10)$$

where $v_p$ is defined as the pulse wave velocity. The term $z(t)$ is the input to the arterial segment under consideration, and not, for example, the aortic pulse pressure waveform. Without knowledge of D and $\Gamma$, it would be difficult to resolve $y(t)$ into forward and reverse components.

Suppose that the disturbance is observed at N sites, separated by a distance d from one another, and that the most distal such site is D millimeters upstream from a reflection site with reflection coefficient $\Gamma$. The total disturbance at the i-th site can be expressed by an equation similar to Eq. (8). If all the components of the observed disturbances are expressed as delayed versions of the forward disturbance observed at the first site, then the disturbance at the n-th site is given by $$y_n(t) = z\left(t - \frac{(n-1)d}{v_p}\right) + \Gamma z\left(t - \frac{(N-1)d}{v_p} - \frac{(N-n)d}{v_p} - \frac{2D}{v_p}\right) \quad (11)$$

for n=1 to N. Equation (11) gives the n-th of N simultaneous equations, which all together may be expressed in matrix form:

$$\begin{bmatrix} y_1(t) \\ \vdots \\ y_n(t) \\ \vdots \\ y_N(t) \end{bmatrix} = \begin{bmatrix} z(t) \\ \vdots \\ z\left(t - \frac{(n-1)d}{v_p}\right) \\ \vdots \\ z\left(t - \frac{(N-1)d}{v_p}\right) \end{bmatrix} + \Gamma \begin{bmatrix} z\left(t - \frac{(N-1)d + 2D}{v_p}\right) \\ \vdots \\ z\left(t + \frac{(n-1)d}{v_p} - \frac{2(N-1)d + 2D}{v_p}\right) \\ \vdots \\ z\left(t + \frac{(N-1)d}{v_p} - \frac{2(N-1)d + 2D}{v_p}\right) \end{bmatrix} \quad (12)$$

This matrix expression allow one to solve for the three unknowns, D, $\Gamma$ and $v_p$. (The quantity d is known from the dimensions of the cMUT patch probe.) However, even though Eq. (12) represents N simultaneous equations in three scalar unknowns, there is still the unknown functional form of z(t) that stands in the way of its solution. This problem is resolved through a Fourier decomposition of z(t). Noting that t will be measured as a discrete time variable in the actual system, the discrete Fourier transform (DFT) is applied to the sampled version of z(t), transforming a finite segment of z(t) into a sequence of frequency components. (The DFT is computed by applying the well-known FFT algorithm.) After this has been done, a matrix equation similar to Eq. (12) is obtained for every coefficient in the computed DFT. Each of these matrix equations will represent N simultaneous equations in four unknowns, three real-valued and one complex-valued. Such an equation, whether underdetermined (for small N) or overdetermined (for large N), can be solved in the least squares sense to obtain an estimate of the pulse wave velocity.

The observed signals $y_n(t)$, for n=1 to N, are composed of linear combinations of delayed versions of z(t), which is a broadband waveform. If one takes the DFT of a segment of a sampled version of $y_n(t)$, it will be possible to express it as a linear combination of the DFTs of z(t). Assuming that one has a segment of samples at times t=0, T, ..., mT, ..., (M−1)T, one can write the DFT as $$Y_n(k) = \sum_{m=0}^{M-1} y_n(mT) e^{-\frac{j2\pi km}{M}} \tag{13}$$

Substituting the definition of $y_n(t)$ from Eq. (10), one obtains $$Y_n(k) = \sum_{m=0}^{M-1} z\left(mT - \frac{(n-1)d}{v_p}\right) e^{-\frac{j2\pi km}{M}} +$$
$$\Gamma \sum_{m=0}^{M-1} z\left(mT - \frac{(n-1)d}{v_p} - \frac{2(N-1)d + 2D}{v_p}\right) e^{-\frac{j2\pi km}{M}}$$
$$= e^{\frac{j2\pi(n-1)dk}{TMv_p}} \sum_{m=0}^{M-1} z(mT) e^{-\frac{j2\pi km}{M}} +$$
$$\Gamma e^{\frac{-j2\pi(n-1)dk + j2\pi(2(N-1)d+2D)}{TMv_p}} \sum_{m=0}^{M-1} z(mT) e^{-\frac{j2\pi km}{M}}$$

Now if one defines the DFT of z(mT) to be Z(k), one has $$Y_n(k) = e^{\frac{j2\pi(n-1)dk}{TMv_p}} Z(k) + \Gamma e^{\frac{-j2\pi(n-1)dk}{TMv_p}} e^{\frac{j2\pi(2(N-1)d+2D)}{TMv_p}} Z(k) \tag{14}$$

Equation (14) is true for n=1, ..., N, and so can be written as a matrix equation, in the form of Eq. (12). Note that neither Z(k) nor the second exponential in the second term of Eq. (14) depends on n, so that the matrix equation is $$Y(k) = Z(k)\varepsilon\left(\frac{2\pi dk}{TMv_p}\right) + \Gamma e^{\frac{j2\pi(2(N-1)d+2D)}{TMv_p}} Z(k)\varepsilon\left(\frac{-2\pi dk}{TMv_p}\right) \tag{15}$$

where $\varepsilon(\phi)$ is a vector defined as $$\varepsilon(\phi) = \begin{bmatrix} 1 \\ \vdots \\ e^{j\phi(n-1)} \\ \vdots \\ e^{j\phi(N-1)} \end{bmatrix} \tag{16}$$

The parameter $\phi$ is referred to herein as the phase increment of $\varepsilon$, since it is the change in phase between successive components of $\varepsilon$. The two phase increments given in Eq. (15) are negatives of one another, and are determined by the sample period, the distance between measurement sites, the DFT coefficient number, the number of samples used in the DFT and the pulse wave velocity. All of these quantities are known except the pulse wave velocity.

Figure 15:
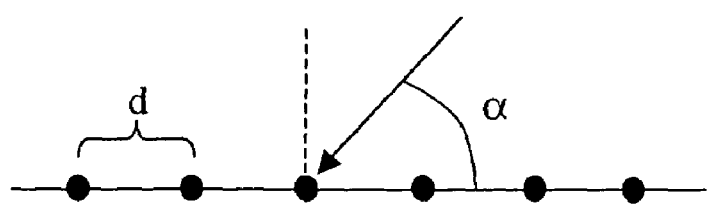
FIG. 15 is a diagram depicting a line array of sensors.

The signal model given by (15) is similar to that encountered in the estimation of far-field directions of arrival (DOA) in array signal processing [D. H. Johnson & D. E. Dudgeon, *Array Signal Processing: Concepts and Techniques*, Prentice-Hall, 1993.]. The phase response of an N-element line array to a narrowband plane wave from angle $\alpha$ can be written as a vector:

$$A\begin{bmatrix} 1 & \cdots & e^{j\frac{2\pi}{\lambda}(n-1)d\cos(\alpha)} & \cdots & e^{j\frac{2\pi}{\lambda}(N-1)d\cos(\alpha)} \end{bmatrix}^T \tag{17}$$

where A is a time-varying complex value representing signal amplitude and phase of the reference element, $\lambda$ is the wavelength of the radiation, and d is the spacing of the array elements. The complete response is the product of (17) and a factor, exp(j$\omega$t), representing the frequency of the planewave. The geometry of the line array is depicted in FIG. 15, where the arrow represents the direction of arrival.

Since the propagation speed is considered to be fixed in the array signal processing problem, we may write the wavelength in terms of a temporal frequency $\omega$ and propagation speed c:

$$\frac{2\pi}{\lambda} = \frac{\omega}{c}.$$

Now we can see that $$Z(k)\varepsilon\left(\frac{2\pi dk}{TMv_p}\right)$$

is equivalent to the phase response vector of (17) with A=Z(k), $$\omega = \frac{2\pi k}{MT},$$

$v_p$=c and $\alpha$=0.

This relationship may be interpreted as follows. In the standard direction-of-arrival problem, the propagation speed is constant and the phase between the components of (17)

varies due to the direction of arrival. In the PWV estimation problem, the direction of arrival is fixed at α=0, while the phase increment varies due to the speed of propagation. Mathematically, this is the same problem, and the same methods of solution apply.

The presence of the reflection term in (15) makes it similar to the symmetric multipath case in array signal processing. Ordinarily, two plane waves from different sources have a random phase relationship to one another; if multiple observations of (17) are made, the factor A will have a different phase for each planewave and for each observation. Such a condition is called an incoherent source distribution. Alternatively, when both planewaves originate from the same signal source (one is typically taken to be a reflected version of the other), they will always have the same phase relationship to each other. This is the case between the two $\epsilon(\phi)$ vectors in (15). This is called a coherent source distribution, and it precludes the use of certain simple estimation procedures, such as the standard MUSIC (Multiple Signal Classification) algorithm without pre-processing. However, there is a great deal of signal processing literature dealing with the DOA estimation problem in this form, and we can now apply it to arterial PWV estimation using long-axis ultrasound.

The MUSIC algorithm operates on an eigendecomposition of the sample covariance matrix of the observations given by Eq. (15). Such operations are well-known in the field of multivariate statistics. The sample covariance matrix for the $k^{th}$ DFT bin is formed by computing:

$$R(k) = \sum_{i=1}^{C} Y_i(k) Y_i^H(k) \tag{18}$$

where C is the number of heart cycles observed, the superscript H stands for Hermitian transposition, and $Y_l(k)$ is defined by Eqs. (13) through (15), and is based on data collected during the l-th heart cycle. Eigendecomposition is a numerical procedure that uses one of a large number of well-known algorithms (such as the QR algorithm using the Householder transform, as described in W. H. Press, et. al. *Numerical Recipes in C*, Cambridge University Press, 1992) to compute eigenvalues and eigenvectors of a matrix. Given the complete set of eigenvalues and associated eigenvectors, and given an assumed number of signals, S (which is equal to 2 in Eq. (15)), the MUSIC algorithm uses a numerical search over all test vectors of the form of Eq. (16) to find those that are most orthogonal to the space spanned by the (N–S) eigenvectors associated with the (N–S) smallest eigenvalues.

In the presence of a coherent reflected pulse, the dimension of the signal space is one rather than two, the value required for successful PWV estimation in the presence of reflections. To address this problem, an alternative method to form a covariance matrix is needed to be able to separate the forward-traveling and backward-traveling pulses. In an exemplary embodiment, the well-known spatial smoothing approach is used, as described in D. H. Johnson & D. E. Dudgeon, *Array Signal Processing: Concepts and Techniques*, Prentice-Hall, 1993, Section 7.3.4.

The spatial smoothing variant of the MUSIC algorithm can be described as follows. The covariance matrix for the spatial smoothing method is formed by averaging covariance matrices from subsets of measurement sites. That is, we form, for the $k^{th}$ DFT bin $$R(k) = \sum_{q=1}^{Q} \sum_{i=q}^{C-Q+q} Y_i(k) Y_i^H(k) \tag{19}$$

where Q is the number of subsets of the measurement sites.

It should be appreciated that spatial smoothing is not the only numerical approach to producing the desired estimate from the data and model given above. In particular, the maximum likelihood, subspace fitting and ESPRIT algorithms can all be applied to PWV estimation. These methods are described, for example, in (H. Krim and M. Viberg, "Two decades of array signal processing research," *IEEE Signal Processing Magazine*, vol. 13, July 1996, pp. 67-94).

The following six steps are executed by the system in order to estimate the pulse wave velocity. The first three steps produce the disturbance measurement, and the last three steps process the disturbance to produce a pulse wave velocity estimate.

Step One: Data Collection and Doppler Shift Estimation.

First, an ultrasound data set is collected, consisting of a small number of I/Q lines, which pass through the artery of interest. These I/Q lines pass through the vessel at right angles to the arterial wall. For example, four or eight lines can be used. (Using more lines works better than using fewer lines.) This data set is taken repeatedly, at regular intervals, so that for each ultrasound line location, an ensemble of ultrasound lines suitable for color flow (mean Doppler shift) processing is available. The pulse repetition frequency for each such ultrasound line will be in the range of 1 to 5 kHz. The frequency of ultrasound used should be in the 8 to 12 MHz range. Since this data is taken repeatedly, an ensemble of any size may be obtained by simply storing in memory an appropriate number of the most recent ultrasound lines. This mode of operation is very similar to color M-mode, which is standard in ultrasound imaging devices. An ensemble may be processed as each new ultrasound line becomes available, or at a lower rate. When Doppler shift estimates are based on ensembles that have significant data in common, the estimates are highly correlated. In the present invention, ensembles will be processed at the highest rate.

Each of the ensembles of ultrasound I/Q lines generated by the data gathering process just described is processed to produce Doppler shift information related to the lateral (with respect to the blood flow direction) motion of the arterial walls. Each of the ensembles will first be filtered by a stationary tissue cancellation (high-pass) filter. This is a standard step in processing of ultrasound data to produce blood flow Doppler information; it is required for arterial wall motion processing because the increase in arterial diameter due to the pulse pressure wave can be quite small. Next, each ensemble will be processed to estimate its mean frequency using the standard autocorrelation method. This is also a standard step in color flow mapping.

The result of the above processing is, for each ultrasound line, a set of Doppler shift estimates: one estimate for each range at which the ultrasound line is sampled. Range samples from the vicinity of the arterial wall closer to the ultrasound probe (the anterior wall) will feature an oscillating Doppler frequency indicating motion towards the probe. This is also true for much of the tissue between the probe and the artery. Range samples from the vicinity of the arterial wall farther from the ultrasound probe (the posterior wall) will produce Doppler data indicating an oscillatory motion away from the probe.

Step Two: Segmentation of the Doppler Shift Data.

The next step in the processing is to segment the Doppler data into two non-overlapping sets of contiguous range samples, one indicating anterior wall motion and the other indicating posterior wall motion. Such a segmentation can be accomplished by averaging the time samples associated with each range sample over some time window of fixed duration. Sites with an average motion toward the probe will be included in one segment and sites with an average motion away will form another. The duration of the time window over which the averaging takes place should be long enough to include at least one heart cycle: a period of 5 seconds duration would be long enough to encompass a single heart cycle at even the slowest heart rate. The segmentation will produce two sets of contiguous range samples, one set representing anterior wall motion and another representing posterior wall motion.

Step Three: Computation of the Observed Disturbance.

Once the segmentation has taken place, each new set of Doppler shift samples can be summed over each segment to produce two distinct quantities, one representing anterior wall motion and the other representing posterior wall motion. The difference between these two quantities $$z_i(t) = \sum_{k \text{ in posterior segment}} x_{i,k}(t) - \sum_{k \text{ in anterior segment}} x_{i,k}(t) \qquad (20)$$

will be called the measured disturbance for the i-th ultrasound line. In Eq. (20), $x_{i,k}(t)$ represents the Doppler shift estimate computed for the i-th ultrasound line (out of four, say) at the k-th range (out of 128, say) at time t. In practice, t is quantized and represents the time of insonification. $z_i(t)$ is an estimate of the time-varying velocity with which the anterior and posterior arterial walls are moving away from each other. This velocity is related to the rate of change of pressure within the vessel and can also relate to arterial wall diameter, and this changing pressure is caused by the passage of the arterial pulse pressure wave.

Step Four: Frequency Decomposition of the Disturbance Observations.

Since z(t) is a random, almost-periodic signal that resembles a sequence of pulses, each period of the observed signal is Fourier transformed separately. Most of the information regarding the relative phase of the N signals will reside in the systolic response. During systole, the disturbance function will behave with the most energy. In order to segment the observations, the peak of one of them (the first ultrasound line, say) is detected and a set of samples is taken that includes some number of samples before and after this point. The resulting segment of recorded samples should represent a time segment whose duration is shorter than a heart cycle. For example, if the subject's pulse rate is 60 beats per minute and the sample rate of the ultrasound lines is 1000 insonifications per second, then it would be reasonable to choose 512 samples around peak systole to compute the DFT. These samples should be chosen so that there are a larger number of samples after peak systole than before, since the disturbance will be asymmetrical in that way.

Note that all N of the disturbance functions must be Fourier transformed for every observed heart cycle. The same set of time samples should be extracted from each for Fourier analysis.

Step Five: Two-step, Least-squares PWV Solution for Each DFT Coefficient.

If a vector of the N Fourier components with index k is formed, that vector will satisfy Eq. (15), according to the model. If the two unknown scalar coefficients of the two $\epsilon(\phi)$ vectors in Eq. (15) are expressed as $b_1$ and $b_2$, one can write Eq. (15) in the compact form $$Y(k) = b_1 \varepsilon(\phi_k(v_p)) + b_2 \varepsilon(\phi_k(-v_p)) = E \begin{bmatrix} b_1 \\ b_2 \end{bmatrix} \qquad (21)$$

where the phase increment in the k-th DFT coefficient due to the pulse wave velocity has been written as $\phi_k(v_p)$ and the N-by-2 matrix E, whose columns are the $\epsilon(\phi)$ vectors, has been defined. Note that the matrix E is a function of the pulse wave velocity.

Now Eq. (21) can be solved for $[b_1 b_2]^T$ as follows:

$$\begin{bmatrix} b_1 \\ b_2 \end{bmatrix} = (E^H E)^{-1} E^H Y(k) \qquad (22)$$

where the superscript H denotes Hermitian transposition. The squared error incurred by using the least-squares model to approximate the observation is $$|Y(k) - E(E^H E)^{-1} E^H Y(k)|^2 = |(I - E(E^H E)^{-1} E^H) Y(k)|^2 \qquad (23)$$

which is a scalar function of the pulse wave velocity. The value of $v_p$ that minimizes Eq. (23) is the estimate of the pulse wave velocity that will be adopted.

In order to compute the pulse wave velocity, values drawn from a range of possible PWVs from 1 to 10 meters per second are used to compute the observation error given by Eq. (23). This range of pulse wave velocities will be called the feasible range. (The Golden Section search is a well-known procedure that can be used to minimize the number of times the expression in Eq. (23) must be evaluated in order to find the minimizing value.) If the minimum observation error is associated with a value in the interior of the feasible range, that value is taken as the PWV estimate for the k-th DFT coefficient vector. If one of the two endpoints of the feasible range minimizes Eq. (23), then the estimate for that DFT index is ignored, since the true minimum is outside the feasible range.

The operation described in this step is performed multiple times, once for each of a range of DFT coefficient indices. Only a relatively small number of indices, corresponding to low-frequency components, need be used for PWV computations. These indices correspond to frequencies at which the power spectral density of the arterial pulse pressure wave is high. In practice, a 512-point DFT with coefficients indexed 3 through 18 has been used.

Alternate Step Five: Covariance Matrix PWV Solution

In an alternate embodiment for step five above, a spatial covariance matrix is formed for a set of narrowband frequency components of a propagating disturbance waveform as described above.

In this embodiment, a vector is formed at a given frequency by selecting the same frequency component from each of the N measurement sites as described in Step 5 above. These vectors are defined by Eq. (15). From this set of vectors for a group of C cardiac cycles, an estimate of the spatial covariance matrix can be found by averaging the outer product of these vectors as in Eq. (19). This computation implements the required spatial smoothing operation.

The spatial covariance matrices are thereafter processed to determine the PWV using well-known signal processing techniques, such as for example the MUSIC (Multiple Signal Classification) algorithm already described.

Once the signal subspace is estimated by eigendecomposition of R, the pulse wave velocities are determined by finding the velocities that are associated with those test vectors that are most orthogonal to the noise subspace (described above with reference to the MUSIC techniques), which is the orthogonal complement of the signal subspace eigenvectors.

Step Six: Combination of the PWV Estimates for Noisy Observations.

When the disturbance waveforms are simply delayed versions of the first-site observation with added reflections (this might be the case in a simulation), the technique above computes the true pulse wave velocity for each DFT index. In actual data, however, the measurements differ from each other due to added noise, the angle that the ultrasound beam makes with the artery and other factors. In this case, a different PWV estimate is obtained for each DFT index, in general. Since anywhere from eight to sixteen (or possibly more) such estimates will be available for each heart cycle, in the case of the least-squares approach, or each group of heart cycles, in the covariance matrix approach, it will be necessary to have a method for combining the estimates into a single overall estimate for each heart cycle or group of heart cycles.

In accordance with one embodiment, the PWV estimates are combined using what is called a trimmed mean. All the feasible estimates (those not at the endpoints of the feasible region) are sorted into numerical order. A number of the largest and the smallest are eliminated, and the remainder are averaged to get the PWV. The number eliminated depends on the number of feasible estimates observed. Alternatively, all the estimates from multiple heart cycles could be combined and processed in this manner to produce a single PWV estimate.

The six steps above, executed repeatedly, produce a sequence of pulse wave velocity estimates at a maximum rate of one per heart cycle. These estimates may be used in the Bramwell-Hill equation, along with arterial area measurements, to estimate blood pressure and/or pulse pressure. In practice, it has been found that estimates from the least-squares approach must be combined over 20 to 30 heart cycles in order to compute meaningful PWV estimates. Because the combination of data in the covariance approach occurs prior to PWV estimation, the final estimate tends to be less noisy than that obtained from the least-squares approach.

Time Corrections

In the description given above, the equations were written as if all N ultrasound lines occurred at the same time. This is not the case. Actually, the insonifications occur in sequence, and there is a time skew between the data collection times. This skew can be accounted for by incorporating it as a fixed delay (for a given n) in Eq. (9). This value, if it is linear in the index n, can be accommodated by modifying the true value of d, the distance between the measurement sites, to one that accounts for the value of the ultrasound time skew. The remainder of the computations can proceed just as before, using this new value of the inter-measurement distance.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A method for monitoring of pressure in an arterial lumen, comprising the following steps:
   (a) converting acquired disturbance propagating waveform information corresponding to energy transmitted and returned from a lumen wall, flow through the lumen and adjacent areas surrounding the lumen, into electrical signals;
   (b) forming at least one spatial covariance matrix of frequency components of the propagating waveform measured at a plurality of locations along the lumen;
   (c) processing the at least one spatial covariance matrix to estimate a velocity of a pulse wave and any reflections traveling through the lumen; and,
   (d) computing the pressure as a function of the estimated velocity.

2. The method as recited in claim 1, wherein the disturbance propagating waveform information is acquired using at least one of an ultrasonic imaging system, a magnetic resonance imaging (MRI) system, a computed tomography (CT) system, and a fluoroscopic X-ray imaging system.

3. The method as recited in claim 1 wherein the lumen is an artery and the computed pressure corresponds to blood pressure through the lumen.

4. The method as recited in claim 3, wherein the computed pressure further corresponds to an indicator of elasticity of the lumen.

5. The method as recited in claim 4, wherein the blood pressure and elasticity are used in the diagnosis in at least one of arterial physiological state or disease.

6. The method as recited in claim 1, wherein step (b) further comprises the following steps:
   estimating a time-varying arterial wall velocity with which respective anterior and a posterior walls of the lumen are moving in relation to one another;
   subjecting the time-varying velocity estimates to Fourier transformation;
   forming vectors of Fourier transformation coefficient indices; and,
   estimating a respective value of the pulse wave velocity that minimizes an observation error for each of a range of Fourier transformation coefficient indices.

7. The method as recited in claim 6, further comprising:
   combining said estimated values of the pulse wave velocity using a trimmed mean algorithm.

8. The method as recited in claim 6 wherein the arterial wall velocity is a measure of at least one of arterial wall velocity or arterial wall diameter.

9. A system for autonomous monitoring of pressure in an arterial lumen, comprising an image acquisition system, data processing means, and means for delivering signals derived from the output of the image acquisition system to said data processing means, wherein said data processing means are programmed to perform the following steps:
   (a) converting acquired disturbance propagating waveform information corresponding to energy transmitted and returned from a lumen wall, flow through the lumen and adjacent areas surrounding the lumen, into electrical signals;

(b) forming at least one spatial covariance matrix of frequency components of the propagating waveform measured at a plurality of locations along the lumen;
(c) processing the at least one spatical covariance matrix to estimate a velocity of a pulse wave and any reflections traveling through the lumen; and,
(d) computing the pressure as a function of the estimated velocity.

10. The system as recited in claim 9, wherein the image acquisition system comprises at least one of an ultrasonic imaging system, a magnetic resonance imaging (MRI) system, a computed tomography (CT) system, and a fluoroscopic X-ray imaging system.

11. The system as recited in claim 9 wherein the lumen is an artery and the pressure corresponds to blood pressure through the lumen.

12. The system as recited in claim 11 wherein the pressure further corresponds to an indicator of elasticity of the lumen.

13. The system as recited in claim 12, wherein the data processing means uses the blood pressure and elasticity in the diagnosis in at least one of arterial health or disease.

14. The system as recited in claim 9, wherein the data processing step (b) further comprises the following steps:
   estimating a time-varying arterial wall velocity with which respective anterior and a posterior walls of the lumen are moving in relation to one another;
   subjecting the time-varying velocity estimates to Fourier transformation;
   forming vectors Fourier transformation coefficient indices; and,
   estimating a respective value of the pulse wave velocity that minimizes an observation error for each of a range of Fourier transformation coefficient indices.

15. The system as recited in claim 14 further comprising:
   combining said estimated values of the pulse wave velocity using a trimmed mean algorithm.

16. The system as recited in claim 14 wherein the arterial wall velocity is a measure of at least one of arterial wall velocity or arterial wall diameter.

* * * * *

UNITED STATES PATENT AND TRADEMARK OFFICE
CERTIFICATE OF CORRECTION

PATENT NO. : 7,425,199 B2
APPLICATION NO. : 10/948434
DATED : September 16, 2008
INVENTOR(S) : Hoctor et al.

It is certified that error appears in the above-identified patent and that said Letters Patent is hereby corrected as shown below:

In Column 16, Line 54, under "Equation 12", delete " $z\left(t - \dfrac{(N-1)d + 2D}{v_p}\right)$ " and insert -- $z\left(t - \dfrac{2(N-1)d + 2D}{v_p}\right)$ --, therefor.

In Column 19, Lines 38-39, delete "suberscript" and insert -- superscript --, therefor.

In Column 25, Line 4, in Claim 9, delete "spatical" and insert -- spatial --, therefor.

Signed and Sealed this

Thirtieth Day of November, 2010

David J. Kappos
*Director of the United States Patent and Trademark Office*